United States Patent [19]

Wang

[11] Patent Number: 4,754,149

[45] Date of Patent: Jun. 28, 1988

[54] OPTICAL PRECIPITATION GAUGE WHICH DETECTS SCINTILLATIONS PRODUCED BY PARTICLE MOVEMENT IN THE LIGHT BEAM

[75] Inventor: Ting-I Wang, Gaithersburg, Md.

[73] Assignee: Scientific Technology, Inc., Rockville, Md.

[21] Appl. No.: 48,389

[22] Filed: May 11, 1987

Related U.S. Application Data

[63] Continuation-in-part of Ser. No. 1,459, Jan. 8, 1987, abandoned.

[51] Int. Cl.$^4$ .............................................. G01N 15/06
[52] U.S. Cl. ..................................... 250/573; 356/442
[58] Field of Search ..................... 250/222.2, 573, 338; 356/442; 340/583

[56] References Cited

U.S. PATENT DOCUMENTS 3,946,286  3/1976  Kinnunen et al. ................... 340/583
4,030,828  6/1977  Sonobe et al. ....................... 356/442

OTHER PUBLICATIONS

Wang et al., "Measurement of Rain Parameters by Optical Scintillation" Applied Optics, vol. 16, pp. 2236–2241, 8/77.
Wang et al., "Simplified Optical Path-Averaged Rain Gauge", Applied Optics, vol. 17, pp. 384–390 2/1/78.
Wang et al., "A Fast-Response Optical Sensor for Measuring Rainfall Rate & Raindrop Size Distribution" C-9-4 pp. 493–495.
Wang et al., "Optical Rain Gauge Using a Divergent Beam", Applied Optics, vol. 19, pp. 3617–3621, 11/1/80.
Wang et al., "Near-Field Laser Disdrometer for Raindrops", Applied Optics, vol. 21, pp. 11–12, 1/1/82.
Wang et al., "Laser Rain Gauge, Near-Field Effect", Applied Optics, vol. 22, pp. 4008–4012, 12/15/83.

"Rainfall Rate Measured Automatically by Processing Scintillation Signals", Laser Focus, 11/77.
Wang et al. "Use of Rainfall Induced Optical Scintillations to Measure Path-Averaged Rain Parameters", J. Optical Soc. of Am vol. 65, No. 8/8/75.
Wang et al. "Measurement of Rain Parameters by Optical Scintillation Comp. Simulation of the Correlation Method," Applied Optics, vol. 16, p. 3176, 12/77.
Wang et al. "Path-Averaged Measurements of Rain Rate and Raindrop Size Dist. Using a Fast-Resp. Optical Sensor", J. of Applied Meteorology, vol. 18, No. 5, 5/79.
Wang et al. "A Laser Rain Gauge" Laser Focus 4/81.

Primary Examiner—David C. Nelms
Assistant Examiner—William L. Oen
Attorney, Agent, or Firm—Charles H. Thomas

[57] ABSTRACT

A precipitation gauge is provided for remotely detecting precipitation and for measuring the rate of precipitation in an open environment, such as an aircraft landing field. The system employs an optical transmitter and receiver, wherein particles of precipitation passing through a light beam from the transmitter cause scintillations at the receiver. The spatial separation between the light transmitter and receiver is quite small, typically substantially less than one meter. The small separation between the transmitter and the receiver is made possible by the use of a partially coherent light beam, in place of a conventional laser beam. The transmitter and receiver are spaced apart a distance of approximately 0.6 meters. The product of one half of the angle of incoherency multiplied by the spatial separation between the transmitter and receiver is preferably about 1.5 millimeters. An output from automatic gain control circuitry is processed by signal processing circuitry and appears as a direct current voltage level which could be either proportional to the rate of precipitation or to the logrithmic rate of precipitation. The precipitation gauge is quite accurate, ranging from extremely light to extremely heavy precipitation rates.

19 Claims, 3 Drawing Sheets

OPTICAL PRECIPITATION GAUGE WHICH DETECTS SCINTILLATIONS PRODUCED BY PARTICLE MOVEMENT IN THE LIGHT BEAM

The present application is a continuation-in-part of U.S. application Ser. No. 001,459, filed Jan. 8, 1987 now abandoned.

BACKGROUND OF THE INVENTION

1. Field of the Invention

The present invention relates to a system for optically and electronically ascertaining the rate of precipitation in ambient air using an unattended instrument.

2. Description of the Prior Art

At present, precipitation rates are conventionally measured by utilizing tipping bucket rain gauges. In such systems a small bucket is exposed to ambient air. When precipitation occurs rain water or melted snow collects in the bucket. When a sufficient amount of precipitation has been collected in the bucket, the bucket will tip, thereby emptying its contents, and triggering a counter. A second bucket is then immediately reset to an upright position to again receive further precipitation. The frequency with which the bucket tips and empties its contents is indicative of the rate of precipitation.

One significant problem in conventional precipitation gauges is that the accuracy of such gauges is quite poor at extremely heavy and extremely light precipitation rates. When precipitation is extremely heavy a significant inaccuracy results due to the time required to mechanically reset the bucket. Conventional tipping bucket rain gauges likewise suffer from considerable inaccuracy at lower precipitation rates due to the evaporation problem and the relatively long resolution time required.

The purpose of providing automated rain gauge measuring systems is to provide for remote monitoring of weather without the necessity for human observation at a site where weather is to be monitored. Automated precipitation rate monitoring allows precipitation conditions at unmanned airfields to be remotely monitored and reported to aircraft in flight.

Automatic rain gauge systems have also been devised which employ laser scintillations and scattering. Such conventional optical rain gauges have utilized optical transmitters employing sources of coherent light, typically laser beams. The spatial separation between the receiver and the transmitter of a conventional laser scintillation detection system is on the order of fifty meters. This large spatial separation between the transmitter and the receiver of an optical rain gauge employing a laser is inconvenient for use in field operation, such as at airports, due to the large area which is required to effectuate automated operation. The ground movement caused by frost or water may also induce pointing problems of the laser beam. Furthermore, such conventional systems are subject to considerable contamination as a result of air turbulence which is likely to occur in ambient air over a distance of fifty meters. As a result, optical rain gauges employing lasers have been utilized to only a very limited degree.

SUMMARY OF THE INVENTION

The present invention is based upon the realization that rain droplet induced optical scintillations can be used to measure rain parameters. When a visible or infrared light beam passes through an irregular medium, the irregularities in the medium produce changes in the wave front. This phenomenon is known as scintillation. The twinkling of stars is a familiar example of such optical scintillations. Different weather conditions produce different signatures of detected scintillations. Raindrop and snowflake induced scintillations can be used to measure rain and snow parameters.

According to the invention, an accurate measure of rate of precipitation is possible in a near field region by transmitting a partially coherent light beam source over a path length on the order of less than one meter which is much shorter than the path length (50 meters) of conventional optical systems employing a fully coherent light beam source, such as a laser. According to the present invention, a partially coherent source, such as an infrared light emitting diode may be used in place of the laser source which conventional optical precipitation gauges have required. A light emitting diode has the advantage of being more reliable than a laser source. In addition, there are no safety regulations governing radiation hazards of light emitting diodes as there are with laser sources. Also, a light emitting diode is much more economical than a laser source.

Due to the variable frequency of electromagnetic radiation from a partially coherent light transmission source, part of the precipitation induced optical scintillation detected by a receiver will be smeared. When a coherent wave front, such as that produced by a laser, meets a sphere, a clear cut disk light shadow will be cast on a receiving plane in the near field region. On the other hand, if a partially coherent wave front meets a sphere, the shadow will be somewhat smeared. The shadow cast is analogous to the creation of an umbra and a penumbra by a celestial eclipse. The type of smearing of the shadow produced by a partially coherent wave front will change the frequency composition of the detected scintillation at the receiving plane. The level of smearing will depend on the extent of coherency of the beam. The optimum receiving band width and the largest allowable inchoherency of the optical source can be ascertained for a specific path length, in the near field region, to measure the rate of precipitation and other rain and snow parameters.

The temporal power spectrum of rain drop induced scintillation of a horizontally oriented line detector is as follows:

$$\omega(f) = \frac{2.6\pi^{3/2} \times 10^{-12} RL \ (2\lambda)^{9/2}}{\Gamma(9/2) \cdot l} \int_0^\infty da \ a^{7/2} \exp(-2\lambda a - 5 \times 10^{-5}\pi^2 f^2 a) \cdot \frac{200\sqrt{a}}{\sqrt{2} \ \pi\theta_o Lf} \ \text{erf}\left(\frac{\sqrt{2} \ \pi\theta_o Lf}{200\sqrt{a}}\right). \tag{1}$$

In the foregoing equation R represents the rain rate, $\theta_o$ is the half angular incoherency of the optical beam, L is the path length, l is the length of the detector, $\lambda = 9/(4\bar{a})$ and $\bar{a}$ is the effective radius of an expotential drop size distribution.

In order to separate the contributions from raindrops and background noise, such as turbulence, wind vibration, fog and haze, a temporal frequency filter is applied to the received signal before the variance measurement is made. To choose this filter, the calibration factor C of the system is defined by the following equation:

$$C = \int_{f_1}^{f_2} df\, w(f)$$

where f1 and f2 are the low and high cut-off frequencies of the bandpass filter.

For an accurate measurement of rate of precipitation, the calibration factor should not be sensitive to different drop sizes. It has been determined (based on Equation (1)) that the product of one-half the angle of incoherency of the light beam multiplied by the distance of separation of the transmitter and the receiver must be between about 0.5 millimeters and about 5.0 millimeters, and is preferably about 1.5 millimeters. A bandpass filter is employed to isolate the outputs in the acceptable frequency range. To fine tune the cutoff frequencies of the bandpass filters, different values of f1 and f2 may be used to calculate the calibration factor for $\theta_o L = 1.5$ millimeters. For rain intensity measurement, a narrow bandpass filter having a band width window of 80 hertz and centered at about 700 hertz is an optimum choice. The value of f1 is then 660 hertz while f2 is 740 hertz. The optimum choice for snow intensity measurement is a narrow bandpass filter having a band width window of 20 hertz, centered at about 150 hertz. The value of f1 is then 140 hertz while f2 is 160 hertz.

In one broad aspect the present invention may be considered to be a precipitation gauge comprising a partially coherent light beam generating transmitter and an optical receiver located in optical communication with the transmitter and in spaced separation therefrom. The light source and distance of separation are such that the product of one-half the angle of incoherency of the light beam, as measured in radians, multiplied by the distance of separation of the transmitter and receiver is between about 0.5 millimeters and about 5.0 millimeters and is preferably about 1.5 millimeters. The precipitation gauge is also comprised of automatic gain control means coupled to amplify signals from the receiver that are generated in response to scintillations occurring in the light beam from the transmitter. Also, a signal processing means is provided to produce an output which is indicative of the rate of precipitation.

According to the invention a precipitation gauge can be designed with a very short length, on the order of 0.6 meters. Also, a partially coherent source such as an infrared light emitting diode (IRED), is used as the transmitting light source. An IRED is more reliable than a coherent source, such as a laser. However, a partially coherent source will also smear out part of the precipitation generated optical scintillation. This kind of smearing will change the frequency composition of the detected scintillations at the receiving plane.

An IRED driver provides an electrical square wave pulse to drive the IRED light source. The light from the IRED is transmitted through a focusing lens as a partially coherent beam, about 50 millimeters in diameter and slighty diverged, to a receiver across a spatial separation on the order of 0.6 meters. The light received by the receiver is transmitted through a horizontal, line aperture in another lens to a photosensitive diode. The photosensitive diode is coupled to a demodulating system, which in turn is coupled to a signal processor. The signal processor produces a logrithmic output having a magnitude proportional to the logrithmic rate of precipitation.

A major advantage of the optical precipitation gauge of the invention over prior mechanical devices is the vastly improved accuracy which is achieved in measuring true instantaneous rainfall over a dynamic range of from less than 0.1 millimeters per hour to more than 1000 millimeters per hour. The precipitation gauge of the invention is so sensitive that it can be used to reliably indicate the presence or absence of precipitation. The fast time resolution, typically 10 seconds, gives continuous, accurate, instantaneous measurements even for very light drizzles. The improved precipitation gauge can accurately measure extremely high rainfall rates where conventional rain gauges fail completely. The precipitation gauge has no mechanical moving parts for the ease of field maintenance. The gauge can also measure rain or snow intensity under subfreezing ambient temperature.

The invention may be described with greater clarity and particularity by reference to the accompanying drawings.

DESCRIPTION OF THE EMBODIMENT

Figure 1:
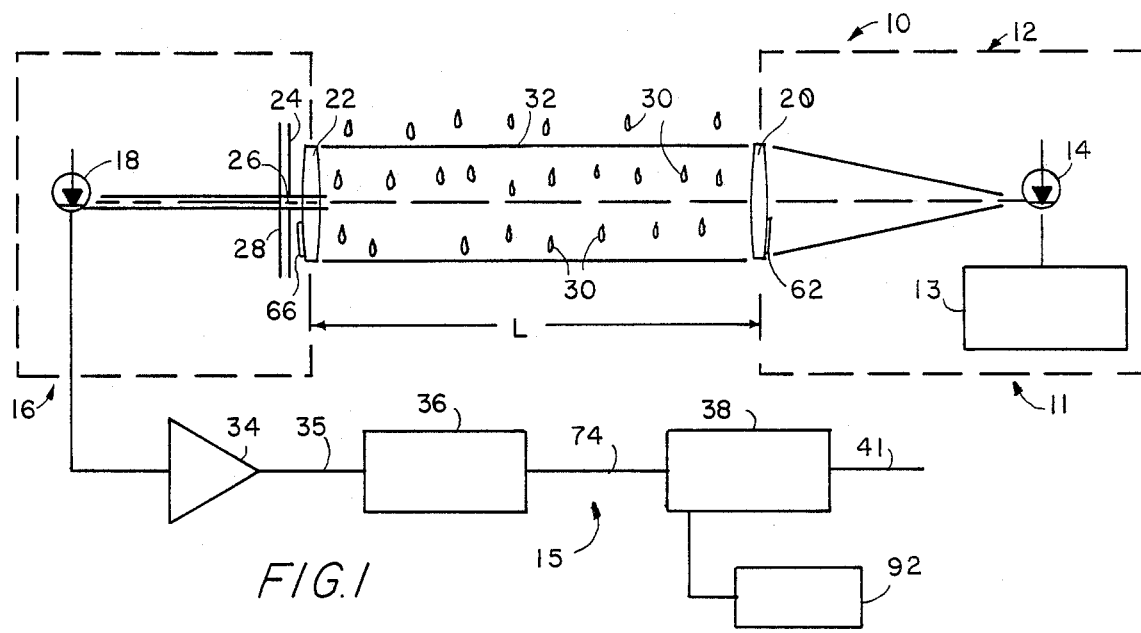
FIG. 1 is a functional block diagram of a preferred embodiment of an optical precipitation gauge according to the invention.

FIG. 1 is a functional block diagram illustrating an optical precipitation gauge indicated generally at 10. The precipitation gauge 10 includes a transmitter 11 and a receiver 15. The transmitter 11 includes both a power supply (not depicted) and a partially coherent light beam source indicated generally at 12 and employing an infrared light emitting diode (IRED) 14. The transmitter 11 includes an IRED modulator 13 which drives the IRED 14. Within the receiver 15 of the precipitation gauge 10 a photosensitive receiver means is indicated generally at 16, and employs a PIN photodiode 18. The receiver 15 physically consists of a receiver lens 22, a preamplifier 34, an automatic gain controlled receiver 36, and a power supply, which is not depicted.

The light beam source 12 of the transmitter 11 includes a 45 millimeter diameter transmitter focusing lens 20 having a focal ratio of F2.0. The infrared emiter die size of the infrared light emitting diode 14 is 0.45 millimeters square.

The receiver means 16 includes a 63 millimeter diameter receiver lens 22, having a focal ratio of F2.4. A mask 24 is located behind the receiver lens 22 and defines a horizont,ally oriented slot 26 which is one millimeter in height. An infrared filter 28 is located behind the mask 24. The active area of the receiving PIN diode 18 is 2.75 millimeters square. The larger receiving divergence angle is desirable to avoid possible signal fluctuations caused by vibration of the mount.

The photosensitive receiver means 16 is positioned a predetermined distance from the partially coherent light beam source 12 and in optical communication therewith. The receiver 16 produces electronic scintillations in response to the movement of particles, such as the precipitation particles indicated at 30, through the partially coherent infrared beam 32 directed from the source 12 toward the receiver means 16. These signals are amplified by a preamplifier means 34, demodulated and filtered in an automatic gain controlled receiver 36, and processed in a signal processor 38 to produce a logrithmic output 41 which is proportional to the rate of precipitation of the particles 30.

The predetermined distance of spatial separation between the receiver means 16 and the light beam source 12 is indicated by the distance L. The spatial separation L of the light beam source 12 and the receiver means 16 is preferably about 0.6 meters. The product of the predetermined distance L multiplied by one-half angle of incoherency of the partially coherent light beam source 12, as measured in radians, must be between about 0.5 millimeters and 5.0 millimeters and is preferably about 1.5 millimeters.

The transmitting lens 20 is equipped with lens heater 62, while the receiving lens 22 is equipped with lens heater 66. The lens heaters 62 and 66 are provided to keep both lenses free of dew. The lens heaters 62 and 66 are bonded to the inside surfaces of their respective lenses.

Figure 4:
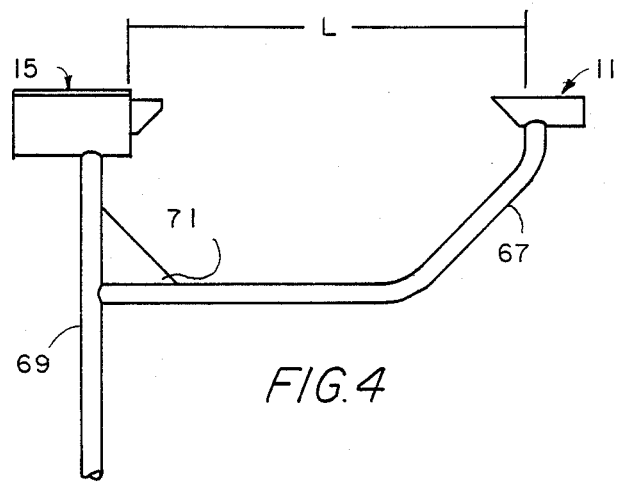
FIG. 4 is a side elevational view of the transmitter and receiver of the preferred embodiment of FIG. 1.

FIG. 4 illustrates the manner in which the transmitter 11 and receiver 15 are physically mounted. As illustrated, the transmitter 11 is a module separate from the receiver 15. The transmitter module 11 and the receiver module 15 are both housed in weather proof enclosures. The transmitter 11 is mounted on the end of a laterally extending arm 67 which is carried from an upright standard 69 and which is supported by a triangular brace plate 71. As is evident from FIG. 4, due to the manner of mounting the distance L between the transmitter and receiver lens is fixed and cannot be accidentally altered.

Figure 2:
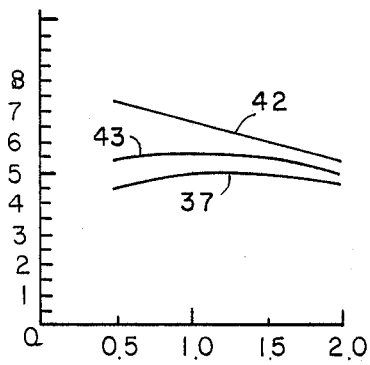
FIG. 2 is a graphical plot of the calibration factor as a function of effective precipitation drop size for various incoherency angles at frequencies between 660 hertz and 740 hertz.

In order to accurately measure rates of precipitation, it is quite important for calibration of the system to be independent of the sizes of the particles of precipitation. FIG. 2 is a graphical illustration, determined based on Equation (1) of the variation of the calibration factor C with droplet size for three different values of $\theta_o L$. In the graph of FIG. 2 the values on the abscissa represent average drop radius in millimeters for different incoherency angles. The values on the vertical ordinate represent the values of the calibration factor C, hereinbefore derived mathematically, for various incoherency angles. The plot of the calibration factor indicated at 42 is for averaged particle radius of between 0.5 and 2.0 millimeters where $\theta_o L$ is equal to zero. The plot 42 indicates that there is a considerable change in the calibration factor where the optical transmitter source produces coherent light. The plot indicated at 37 likewise shows some variations in the calibration factor when the particle drop size ranges between 0.5 and 2.0 millimeters and where $\theta_o L = 2$ millimeters. The least variation in the calibration factor was achieved when $\theta_o = 1.5$ millimeters, and the plot of the calibration factor for this condition is indicated at 43 in FIG. 2. Thus, it has been determined that a value of $\theta_o L = 1.5$ millimeters is the preferred choice to obtain accurate precipitation rate measurements.

Figure 3:
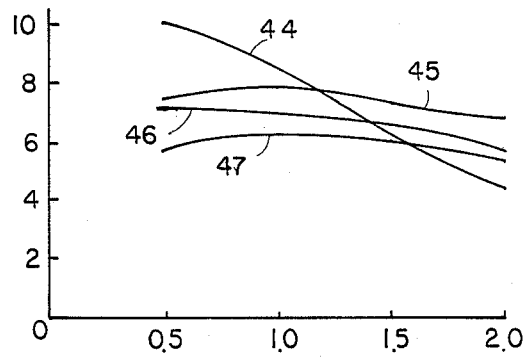
FIG. 3 is a graphical plot of the calibration factor as a function of effective precipitation drop size for various frequency bands.

It is also important to avoid the introduction of errors due to precipitation drop size by an improper selection of a frequency of interest in the receiver 15. FIG. 3 illustrates graphically the variation of the calibration factor where $\theta_o L = 1.5$ millimeters with the signal bandpass window set at different frequencies. The numbers on the abscissa of FIG. 3 indicate average precipitation drop size measured in millimeters. The numbers on the vertical ordinate of FIG. 3 illustrate the calibration factor where $\theta_o = 1.5$ millimeters and when the bandpass window of the signal processor is set at different frequency ranges.

At a value of $\theta_o = 1.5$ millimeters, the plot of the calibration factor for precipitation drop radius between 0.5 and 2.0 millimeters as measured at 1500 hertz with a frequency window width of 150 hertz is indicated at 44. The plot of the calibration factor for the same droplet size range measured between 200 and 1500 hertz is indicated at 45. The plot between the same precipitation drop sizes as measured between 300 and 2000 hertz is indicated at 46. The most uniform calibration factor for precipitation drop sizes between 0.5 and 2 millimeters was obtained at a frequency of 700 hertz plus and minus 40 hertz, and the plot at that frequency is indicated at 47. As a result, it was determined that a narrow bandpass filter 80 hertz in width and centered at 700 hertz for $\theta_o L = 1.5$ millimeters is the ideal choice for rain intensity measurements. For snow intensity measurements, it was determined empirically that a narrow bandpass filter 20 hertz in width and centered a 150 hertz is the optium choice.

FIGS. 5 through 10 are schematic diagrams of the electronic circuitry employed to produce the optical beam 32 and to detect and process scintillations occurring between the transmitter 11 and the receiver 15 to produce an output indicative of rate of precipitation. One major concern of the system design is that the signal detected by the receiver means 16 of FIG. 1 must have a sufficient signal to noise ratio under various background lighting conditions. Background light contamination results from natural ambient lighting conditions, such as sunshine, and also from man-made lighting conditions, such as street lighting, floodlighting and the like. The infrared light emitting diode 14 is thxrefore driven by the modulator 13 to ensure that the system is immune to background noise.

The carrier frequency generated by the modulator 13 must be much higher than the frequency band of interest. It has been determined that very limited energy of precipitate induced scintillation lies above 1 kilohertz. Therefore, the IRED modulator 13 generates a carrier frequency of at least 2 kilohertz and preferably 50 kilohertz.

Figure 5:
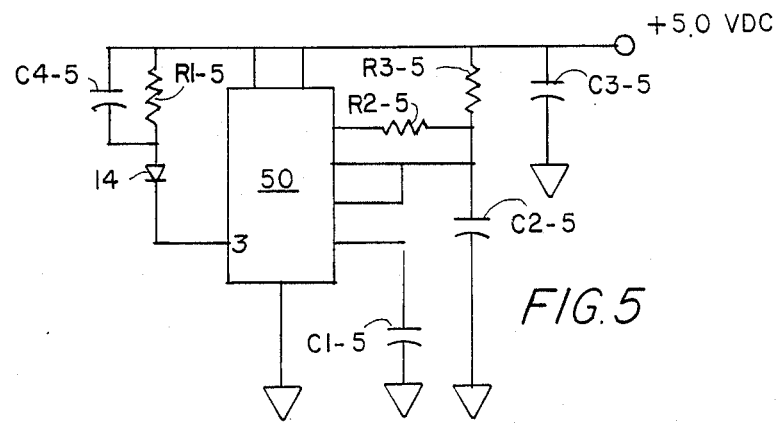
FIG. 5 is a schematic diagram of the transmitter modulation circuit employed in the preferred embodiment of FIG. 1.

FIG. 5 illustrates schematically the circuitry employed in the modulator 13. Specifically, the modulator 13 employs a 555 timing oscillator indicated at 50. The square wave pulse output at pin 3 of the timer 50 is connected to drive the IRED 14 with 50% duty cycle square wave modulation. The values of the resistors and capacitors employed in FIG. 5 to produce the desired output to the IRED 14, as well as the values of all of the resistors and capacitors and other component specifications in FIGS. 6–10, are set forth in Table 1 at the conclusion of this description of the preferred embodiment.

As hereinbefore noted, the infrared light emitted from the IRED 14 is collected by the focusing lens 20 to form a partially coherent beam 32 about 50 millimeters in diameter. The beam 32 diverges slightly. The light beam 32 is pointed toward the receiving lens 22 of the receiver 16 which is located 0.6 meters from the transmitting lens 20. The precipitation particles 30 falling through the beam 32 will modulate the beam to cause intensity scintillations in the received light signal. The optical assembly of the receiver means 16 employs the mask 24 having the horizontal line aperture 26 so as to discriminate vertical motion to the horizontal motion of the precipitation particles 30 as they pass through the beam 32. The modulated light from the transmitter 11 is detected by the PIN photodiode 18, illustrated in FIGS. 1 and 6, which is coupled to the preamplifier 34 and the automatic gain controlled receiver 36. The automatic gain controlled receiver 36 acts as a normalizer to overcome the problems associated with received power fluctuations caused by temperature change, component aging, dust on the lenses 20 and 22 and the obscuring effects of fog or haze. The output of the automatic gain controlled receiver 36 is demodulated and passed to the signal processor 38.

Because the transmitter light source 12 and the photosensitive receiver module 16 are exposed to ambient weather conditions, it is extremely important to the proper operation of the system for both of the lenses 20 and 22 to be free of condensed water and frost. For this purpose, heaters 62 and 66 are bonded to the insides of each lens. The transmitter heater is indicated at 62 and the receiver heater is indicated at 66 in FIG. 1. Since light transmitted through the receiver lens 22 is blocked except at the narrow horizontal slot 26, the heater 66 can cover all but a one-half inch horizontal strip through the centers of each of the lenses 20 and 22. The heater 62 for the transmitting lens 20 is located below the clear area of that lens. Likewise, the heater 66 for the receiving lens 22 is located below the clear area.

Positive temperature coefficient thermisters have been chosen for lens heaters 62 and 66. The thermister increases its resistance when the temperature rises and therefore consumes less electricity. The selection of thermisters as heaters will save the overall system power consumption which is critical for battery or solar panel operation.

The IRED 14 is preferably a GE/F5E1 infrared emitter, which is rated 12 milliwatts CW at 880 nanometers. The die size through which light is directed to the lens 20 is 0.45 millimeters square. It has been determined that $\theta_o L$ should be about 1.5 millimeters to insure linearity of calibration. The transmitting lens 20 is a 45 millimeter diameter F2.0 lens. The foregoing transmitter specifications yield a $\theta_o L$ equal to 1.5 millimeters, where the distance L is equal to 0.6 meters.

The receiving lens 22 is a 63 millimeter diameter F2.4 lens. Behind the receiving lens 22 there is a mask 24 which defines the 1 millimeter high horizontally oriented slot 26. An infrared filter 28 is located behind the mask 24. A model BPX1 PIN photodiode 18 with an active area of 2.75 millimeters square is used.

Figure 6:
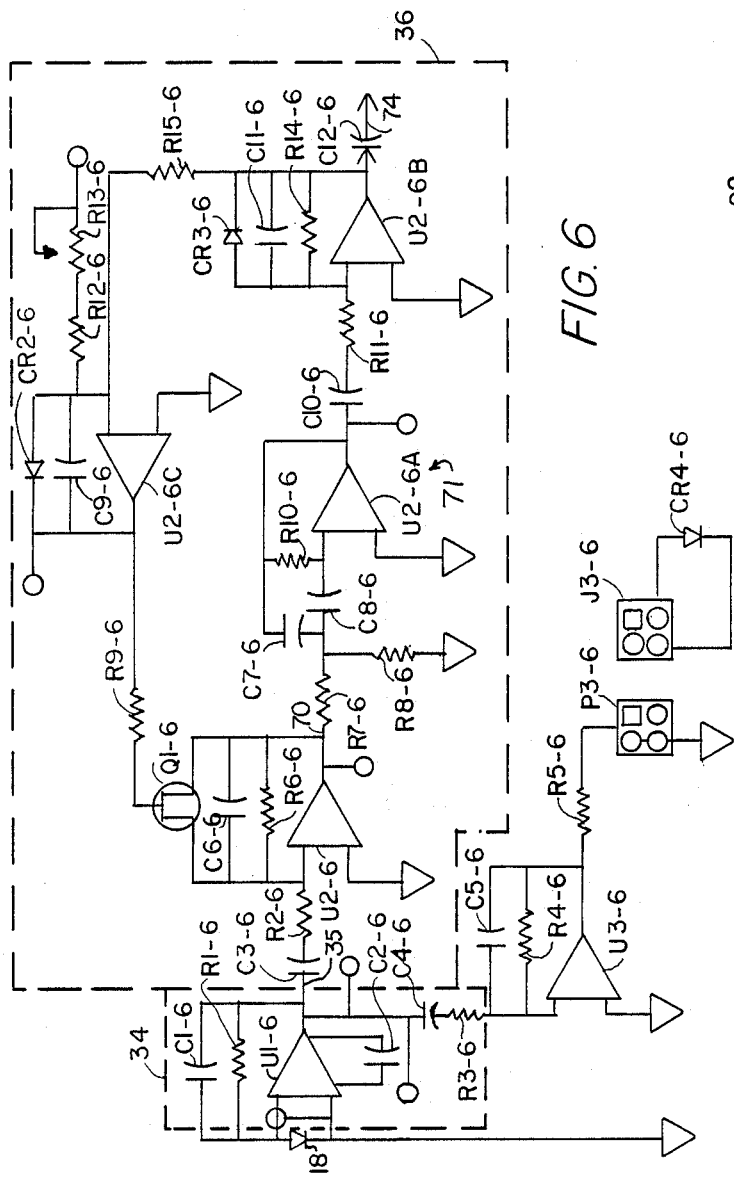
FIG. 6 is a schematic diagram of the automatic gain control circuit of the receiver of the preferred embodiment of FIG. 1.

FIG. 6 illustrates the model BPX61 photodetector 18 and the preamplifier and automatic gain controlled receiver schematics. As illustrated in FIG. 6, the output of the PIN photodiode 18 is coupled to the preamplifier 34, which includes a low noise, current to voltage amplifier U1-6. The photodiode 18 is operated unbiased in the photovoltaic mode to capitalize on its excellent linearity. The output of the preamplifier 34 appears at 35 and is provided as an input to the automatic gain controlled receiver 36.

The input signal to the automatic gain controlled receiver 36 from the preamplifier 34 appears on line 35 and is passed to a FET controlled gain amplifier U2-6. The amplifier U2-6 is controlled by a P-channel FET Q1-6 and amplifies the signal from line 35 by a factor of 20. The output of amplifier U2-6 appears on line 70, where it is amplified further by a bandpass filter 71 which includes a filtering amplifier U2-6A. Ampliifer U2-6A is a bandpass amplifier centered at 50 kilohertz with a window width of 5 kilohertz. The bandpass filter 71 is a 50 kilohertz bandpass filter which cleans the received signal and feeds the carrier signal to a rectifying amplifier U2-6B. The output of the rectifying amplifier U2-6B is integrated by an integrating amplifier U2-6C. The output of the integating amplifier U2-6C is used to control the FET Q1-6. The integrating amplifier U2-6C thereby provides an automatic gain controlled loop.

The output 35 from the preamplifier 34 is also directed to an LED driving amplifier U3-6. The output of driving amplifier U3-6 is directed to a plug P3-6 to which a jack J3-6 is releasably coupled. The output of the LED driving amplifier U3-6 is used to drive a green light emitting diode CR4-6. Illumination of the diode CR4-6 indicates to an observer receipt of sufficient signal from the transmitter 11 from which a rain rate or snow intensity indication may be derived. The diode CR4-6 is used to determine whether or not a system major failure has occurred.

Figure 7:
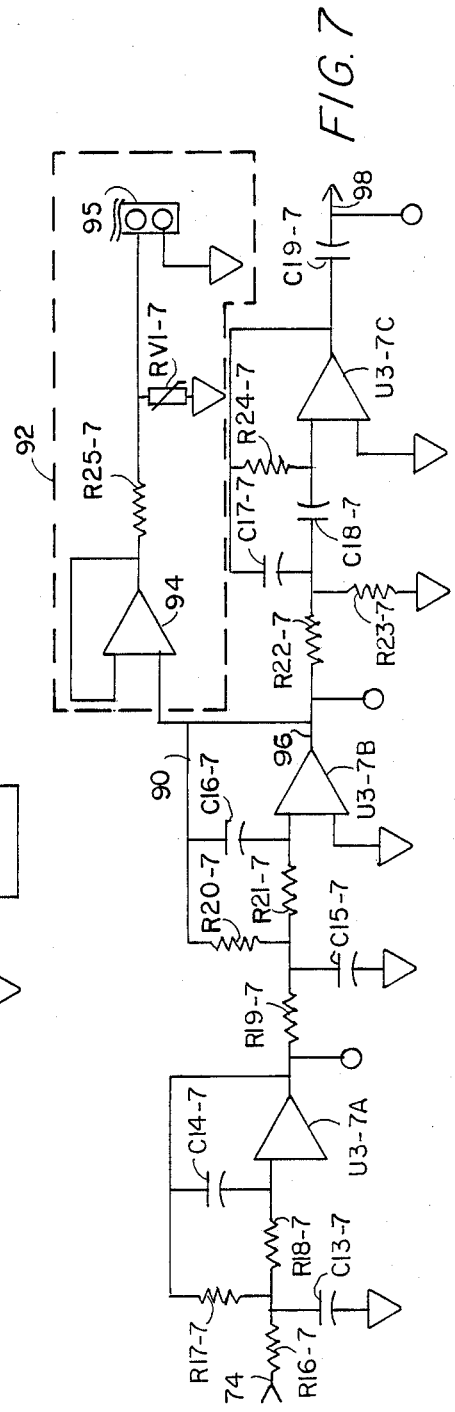
FIG. 7 is a schematic diagram of a portion of the signal processor of the preferred embodiment of FIG. 1.
Figure 8:
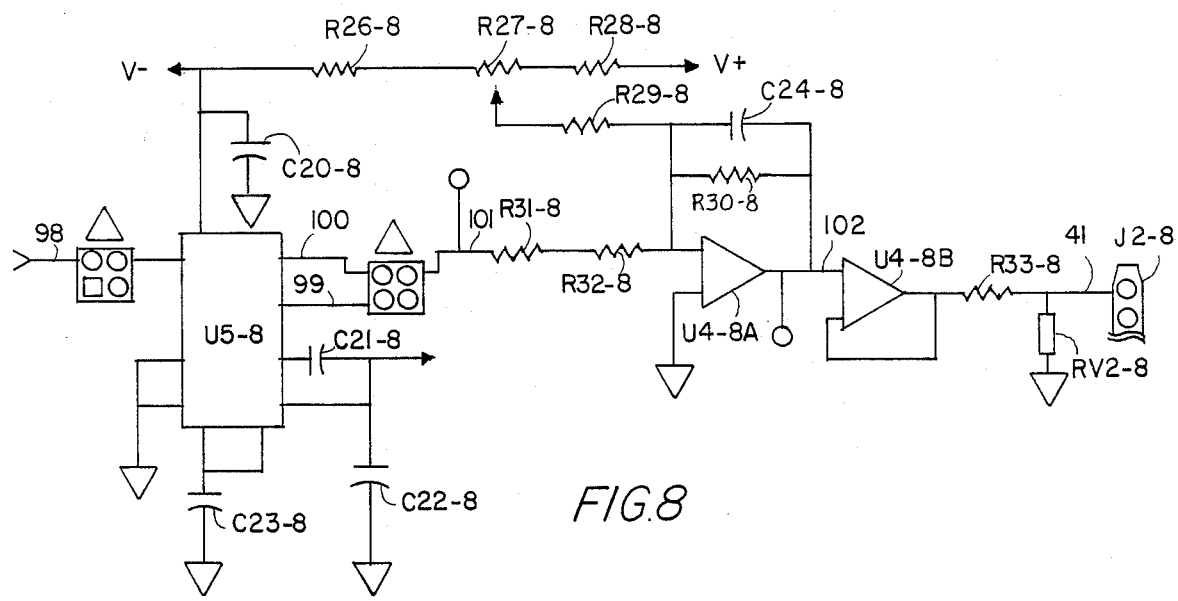
FIG. 8 is a schematic diagram of the remaining portion of the signal processor of the preferred embodiment of FIG. 1.

The output of the automatic gain controlled receiver 36 appears on line 74 and is provided as an input to the signal processer 38, which is depicted schematically in FIGS. 7 and 8. The input on line 74 to the signal processor 38 is first directed through low pass filtering amplifiers U3-7A and U3-7B which are used to cut off the carrier frequency. Prior to reaching the carrier filtering amplifier U3-7B, the carrier signal is passed on line 90 to a monitor indicated at 92. The signal on line 90 is directed to a buffer amplifier 94 which monitors the system for precipitation particles induced optical scintillation signals.

It is to be understood that the monitor 92 is an optional feature, which may or may not be desired by the user. Operation of the signal processor 38 of FIG. 1 does not depend upon the presence of the monitor 92 for proper operation.

The output of the lowpass filtering amplifier U3-7B appears on line 96 and is directed to a signal filtering amplifier U3-7C. The output signal from the filtering amplifier U3-7C is biased to pass a signal of 700 hertz, plus or minus 40 hertz.

The filtered output on line 98 of FIG. 7 appears as an input in FIG. 8 to the root mean square to DC voltage converter U5-8. The voltage converter U5-8 produces both a linear output on line 99 and a logrithmic output on line 100. Either output may be employed to indicate the rate of precipitation. In the preferred arrangement however, it is the logrithmic output on line 100 which is taken on line 101. This output is passed as an input to an amplifier U4-8A which steps up the signal gain. The output of the amplifier U4-8A on line 102 is directed to a buffer amplifier U4-8B. The amplifier U4-8A is an integrating amplifier with a ten second time constant. The log output of the converter U5-8 is used to improve the overall dynamic range of the system. The output of the integrating amplifier U4-8A is a direct current voltage level. Through the buffer amplifier U4-8B this output appears as the signal 41 in FIG. 1 to a jack connection J2-8 in FIG. 8. The signal on line 41 is logrithmically proportional to the rate of rainfall or snowfall averaged over the most recent 10 second period.

Figure 9:
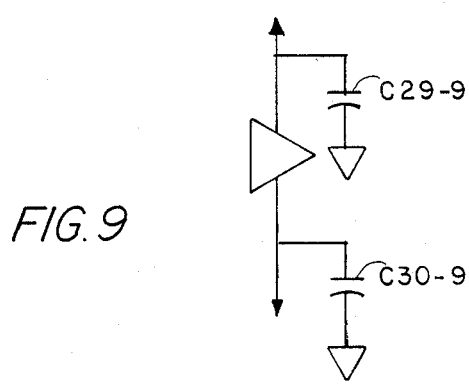
FIG. 9 illustrates the power connections to one of the operational amplifiers depicted in FIGS. 6–8.
Figure 10:
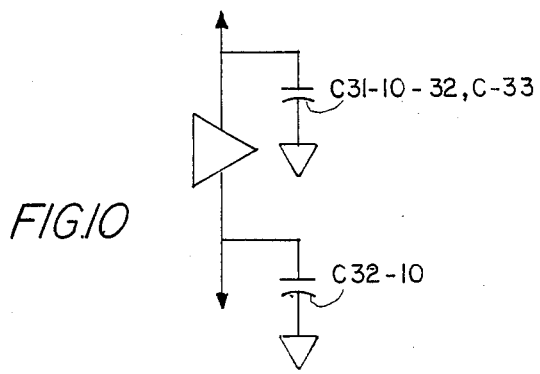
FIG. 10 illustrates the power connections to the other operational amplifiers depicted in FIGS. 6–8.

FIG. 9 illustrates the power connections for amplifier U1-6 depicted in FIG. 6, while FIG. 10 illustrates the power connections for all other amplifiers depicted in FIGS. 6 through 8. The capacitors indicated in FIGS. 9 and 10 aid in cleaning up power inputs to the associated amplifiers.

Undoubtedly, numerous variations and modifications of the invention will become readily apparent to those familiar with conventional rain guage systems. Accordingly, the scope of the invention should not be construed as limited to the specific embodiment thereof depicted and described herein, but rather is defined in the claims appended hereto.

TABLE 1

| | |
|---|---|
| R1-5 | 10 K ohms |
| R2-5 | 2.1 K ohms |
| R3-5 | 5.11 K oms |
| C1-5 | .01 microfarads |
| C2-5 | .0027 microfarads |
| C3-5 | 10 microfarads |
| C4-5 | .047 microfarads |
| R1-6 | 221 K ohms |
| R2-6 | 2.49 K ohms |
| R3-6 | 1.21 K ohms |
| R4-6 | 221 K ohms |
| R5-6 | 150 ohms |
| R6-6 | 100 K ohms |
| R7-6 | 9.53 K ohms |
| R8-6 | 1 K ohms |
| R9-6 | 100 K ohms |
| R10-6 | 9.53 K ohms |
| R11-6 | 10 K ohms |
| R12-6 | 301 K ohms |
| R13-6 | 1 M ohms variable |
| R14-6 | 100 K ohms |
| R15-6 | 72 K ohms |
| C1-6 | 15 picofarads |
| C2-6 | 18 picofarads |
| C3-6 | .01 microfarads |
| C4-6 | 0.1 microfarads |
| C5-6 | 5 picofarads |
| C6-6 | 5 picofarads |
| C7-6 | 330 picofarads |
| C8-6 | 330 picofarads |
| C9-6 | 47 microfarads |
| C10-6 | .01 microfarads |
| C11-6 | 5 picofarads |
| C12-6 | 1.0 microfarads |
| CR2-6 | IN270 |
| CR3-6 | IN270 |
| CR4-6 | LN31GP.HL |
| R16-7 | 8.06 K ohms |
| R17-7 | 15.8 K ohms |
| R18-7 | 5.36 K ohms |
| R19-7 | 22.6 K ohms |
| R20-7 | 56.2 K ohms |
| R21-7 | 16.2 K ohms |
| R22-7 | 4.02 K ohms |
| R23-7 | 30.1 K ohms |
| R24-7 | 30.1 K ohms |
| R25-7 | 51.1 K ohms |

TABLE 1-continued

| | |
|---|---|
| C13-7 | .027 microfarads |
| C14-7 | .0047 microfarads |
| C15-7 | .0068 microfarads |
| C16-7 | .001 microfarads |
| C17-7 | .022 microfarads |
| C18-7 | .022 microfarads |
| C19-7 | 1.0 microfarads |
| RV1-7 | 22Z3 |
| RV2-8 | 22Z3 |
| R26-8 | 95 K ohms |
| R27-8 | 50 K ohms, variable |
| R28-8 | 75 K ohms |
| R29-8 | 301 K ohms |
| R30-8 | 301 K ohms |
| R31-8 | 8.25 K ohms |
| R32-8 | 490 ohms |
| R33-8 | 51.1 ohms |
| C20-8 | .1 microfarads |
| C21-8 | 10 microfarads |
| C22-8 | .1 microfarads |
| C23-8 | .1 microfarads |
| C24-8 | 33 microfarads |
| C29-9 | .1 microfarads |
| C30-9 | .1 microfarads |
| C31-10 | .1 microfarads |
| C32-10 | .1 microfarads |

We claim:

1. A precipitation gauge comprising a partially coherent light beam source, photosensitive receiver means positioned a predetermined distance from said partially coherent light beam source and in optical communication therewith to produce electronic signals in response to scintillations caused by particle movement between said source and said receiver means, wherein the product of said predetermined distance and one-half the angle of incoherency of said partially coherent light beam source is between about 0.5 millimeters and about 5.0 millimeters, and automatic gain control means for producing an output indicative of rate of precipitation.

2. A precipitation gauge according to claim 1 wherein said product of said predetermined distance and one-half the angle of incoherency of said partially coherent light beam source is about 1.5 millimeters.

3. A precipitation gauge according to claim 1 wherein said automatic gain control means includes a bandpass filter defining a frequency window of between about 660 hertz and about 740 hertz.

4. A precipitation gauge according to claim 1 wherein said partially coherent light beam source is comprised of an infrared light emitting diode.

5. A precipitation gauge according to claim 4 wherein said partially coherent light beam source is further comprised of a 45 millimeter diameter transmitter lens having a focal ratio of F2.0.

6. A precipitation gauge according to claim 5 wherein said photosensitive receiver means is comprised of a 63 millimeter diameter receiver lens having a focal ratio of F2.4, a mask defining a horizontal slot about one millimeter in height located behind said receiver lens, an infrared filter located behind said mask, and a photodiode detector.

7. A precipitation gauge according to claim 6 further comprising electrically powered heating means for both of said lenses.

8. A precipitation gauge according to claim 7 wherein each of said heating means uses positive temperature coefficient thermisters.

9. A precipitation gauge according to claim 1 wherein said light beam source is driven at a carrier frequency of at least about 2 kilohertz, and further comprising a signal processing means coupled to receive an output from said automatic gain control means, and said automatic gain control means includes a plurality of amplification stages controlled by said carrier frequency, and said signal processing means includes a root mean square to direct current converter which produces an output signal that is proportional to the rate of precipitation.

10. A precipitation gauge according to claim 1 wherein said light beam source is driven at a carrier frequency of at least about 2 kilohertz, and further comprising a signal processing means coupled to receive an output from said automatic gain control means, and said automatic gain control means includes a plurality of amplification stages controlled by said carrier frequency, and said signal processing means includes a root mean square to direct current converter which produces an output signal that is proportional to the logrithmic rate of precipitation.

11. A precipitation gauge comprising: a partially coherent light beam generating transmitter, an optical receiver located in optical communication with said transmitter and in spaced separation therefrom such that the product of one-half the angle of incoherency of said light beam multiplied by the distance of separation of said transmitter and said receiver is between about 0.5 millimeters and about 5.0 millimeters, automatic gain control means coupled to amplify signals from said receiver generated in response to scintillations occurring in said light beam from said transmitter, and signal processing means for producing an output indicative of rate of precipitation.

12. A precipitation gauge according to claim 11 further characterized in that said spaced separation of said transmitter and said receiver is about 0.6 meters.

13. A precipitation gauge according to claim 12 further characterized in that said product of one-half said angle of incoherency multiplied by said distance of separation is about 1.5 millimeters.

14. A precipitation gauge according to claim 13 wherein said automatic gain control means includes a band pass filter for passing frequencies between about 660 hertz and about 740 hertz to said signal processor.

15. A precipitation gauge according to claim 11 further characterized in that said transmitter is comprised of an infrared light emitting diode.

16. A precipitation gauge according to claim 15 wherein said transmitter includes a die having a die size about 0.45 millimeters square and said transmitter is further comprised of a focusing lens which produces a partially coherent light beam about 50 millimeters in diameter.

17. A precipitation gauge according to claim 11 wherein the product of one-half the angle of incoherency of said light beam multiplied by the distance of separation of said transmitter and said receiver varies by no more than 15 percent.

18. A precipitation gauge according to claim 11 in which said automatic gain control means includes a band pass filter which defines a band pass frequency width of 80 hertz centered at a frequency of 700 hertz.

19. A precipitation gauge according to claim 11 in which said transmitter and said receiver are both equipped with focusing lenses and further comprising electrical heating means for heating both of said lenses.

* * * * *